United States Patent
Mordukhovich

(12) 
(10) Patent No.: US 6,656,332 B1
(45) Date of Patent: Dec. 2, 2003

(54) REPLICATING METHOD FOR SURFACE FINISH INSPECTION

(75) Inventor: Gregory Mordukhovich, Bloomfield Hills, MI (US)

(73) Assignee: General Motors Corporation, Detroit, MI (US)

( * ) Notice: Subject to any disclaimer, the term of this patent is extended or adjusted under 35 U.S.C. 154(b) by 0 days.

(21) Appl. No.: 10/157,475

(22) Filed: May 29, 2002

(51) Int. Cl.[7] .................. C23C 14/34; B05D 1/36; B05D 7/00; G01N 19/02; G01B 5/28
(52) U.S. Cl. .............. 204/192.13; 204/192.15; 427/9; 427/403; 427/407.1; 427/404; 427/414; 73/104; 73/105; 73/865.8
(58) Field of Search ............. 204/192.13, 192.15; 427/9, 403, 407.1, 414, 404; 73/104, 105, 865.8

(56) References Cited

U.S. PATENT DOCUMENTS

| | | | |
|---|---|---|---|
| 4,198,362 A | * | 4/1980 | Ticker et al. .......... 264/40.1 |
| 4,576,850 A | * | 3/1986 | Martens ............... 428/156 |
| 5,623,375 A | * | 4/1997 | Floch et al. ........... 359/883 |

* cited by examiner

*Primary Examiner*—Steven H. VerSteeg
(74) *Attorney, Agent, or Firm*—Leslie C. Hodges

(57) ABSTRACT

A method of inspecting the surface finish of a component comprising providing an original surface to be inspected. A release agent is applied onto the original surface and an epoxy mixture is applied over the release agent. The epoxy mixture is allowed to harden into a replicated surface. Once the epoxy mixture has hardened, the replicated surface is removed and a metallic coating is applied thereon. The coated replicated surface is then ready for inspection.

9 Claims, 2 Drawing Sheets

REPLICATING METHOD FOR SURFACE FINISH INSPECTION

TECHNICAL FIELD

This invention relates to a method of inspecting a hard-to-access surface area of a component.

BACKGROUND OF THE INVENTION

There are many available techniques for inspecting metal surfaces such as optical microscopes and profilers having styluses. These methods work well for inspecting rolled steel or large surface areas where microscopes, cameras, and styluses are accessible. However, these techniques do not work well when inspecting the metal on internal surfaces or other hard-to-access areas such as gear teeth. Direct optical surface finish measurement of fine pitch gears is difficult because of line-of-sight problems. The adjacent tooth prevents the surface positioning perpendicular to the light beam. Angular positioning leads up to 20% loss of the reflected light. Replicas became necessary for fine pitch gears to get surface finish inspection without gear destruction. Further, these methods frequently require that a portion of the surface to be inspected be cut from the main article of manufacture and is thus destructive. A non-destructive method is therefore necessary to monitor accumulative damage.

Accordingly, an epoxy-based replicating technique was developed. The technique involves applying a petroleum distillate, which contains 10 to 12 chain-linked hydrocarbons, to the surface to be inspected. Finely ground charcoal must be mixed with the epoxy to provide proper reflective quantities. The mixture is then applied to the surface. After the mixture hardens, the replicated surface is removed and inspected. This technique has certain drawbacks. The ratio of ingredients must be precise or the replicated surface will not have proper reflective qualities. Further, if the mixture is not completed in 30 seconds, the replicating properties are sharply reduced. Accordingly, a new replicating technique is needed.

SUMMARY OF THE INVENTION

Accordingly, it is an object of this invention to provide an improved method of inspecting a surface in inaccessible areas without damaging the original article of manufacture and that does not depend on precise ratios of ingredients.

The present invention overcomes a compromised encountering of prior art by providing a method for inspecting the surface finish of a component by first providing an original surface. A release agent is then applied to the original surface. An epoxy mixture is then applied onto the original surface over the release agent. After the epoxy mixture hardens into a replicated surface, it is removed. A metallic coating is then applied to the replicated surface and the replicated surface is then inspected.

In another embodiment of the invention, the epoxy mixture comprises charcoal.

In yet another embodiment of the invention, the step of applying metallic coating comprises sputtering a metallic coating of gold, aluminum, or silver.

DESCRIPTION OF THE PREFERRED EMBODIMENT

Figure 1:
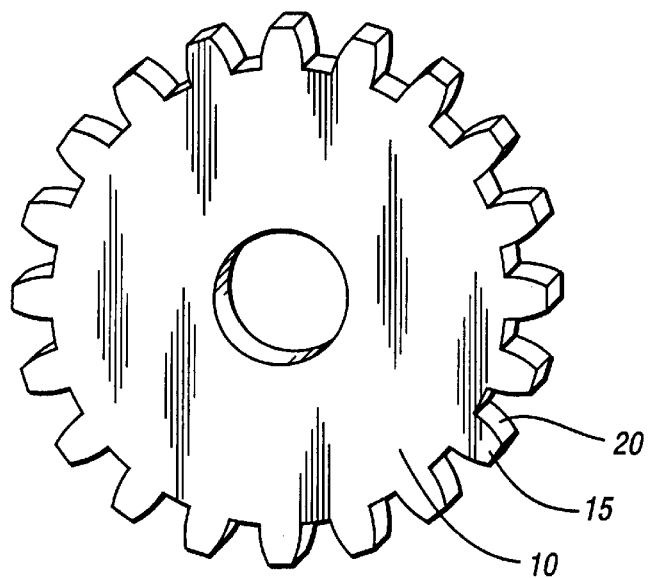
FIG. 1 is a perspective view of a gear having a surface to be inspected.
Figure 2:
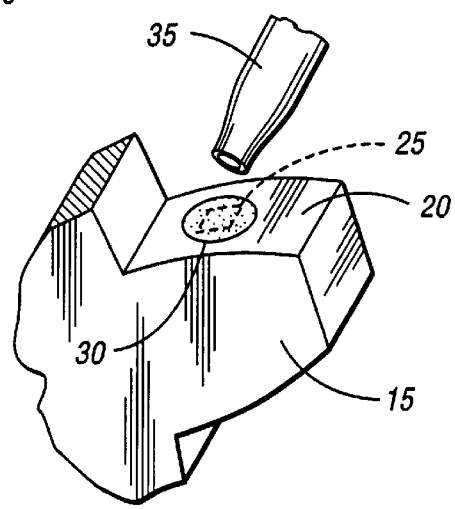
FIG. 2 is a fragmentary view of the gear in FIG. 1 to show a release agent being applied to the surface of a gear tooth.

Referring now to FIG. 1, a gear 10 has a plurality of teeth 15. In this example, the inside surface 20 of a tooth 15 is sought to be inspected in a non-destructive manner. Such inspection is critical to evaluate the gear manufacturing process and to evaluate the degradation of the gear caused by actual use. Because of the configuration of the teeth 15, it is generally not possible to simply remove the gear and inspect it. Accordingly, a replica of that inside surface must be made and inspected.

An inspector locates an imaginary target spot 25 on inner surface 20 of the tooth 15 for inspection. The spot 25 is picked as an original surface so that it can be consistently and repeatedly found for inspection or testing throughout the life of a particular gear or for comparing one gear to another gear. A release agent 30 is applied over the target inspection spot 25 using, for example, an eyedropper 35. Various release agents can be used. Preferably, the release agent is a petroleum distillate containing aromatic and aliphatic hydrocarbons.

Figure 3:
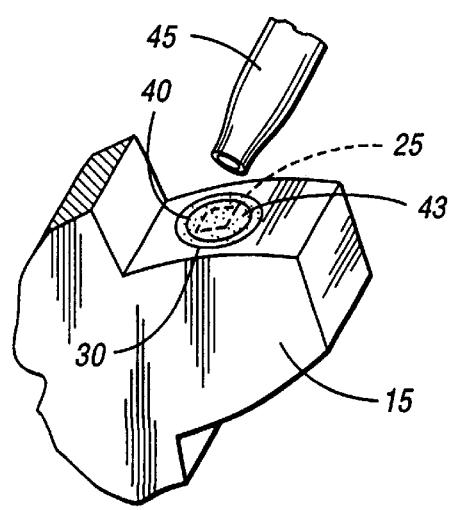
FIG. 3 is a fragmentary view like FIG. 2 to show an epoxy being applied to the release agent.

Referring now to FIG. 3, an epoxy mixture 40 is applied on top of the release agent 30 which had been applied over the original surface. The epoxy mixture may be any commercially available epoxy. Preferably, the epoxy has a one-to-one ratio of resin to hardener. Similar to the release agent, the epoxy mixture may be applied by an eyedropper 45. The epoxy mixture is applied within the confines of the underlay of release agent so that the epoxy mixture will not adhere to the tooth 15.

Charcoal 43 may be added to the epoxy mixture to provide some reflective characteristics for the replica. Preferably, the epoxy mixture will contain approximately 5% charcoal by volume but may also contain 0% to 30% charcoal by volume. Additionally, any powder that provides reflective qualities can be used in the same ratios.

The epoxy mixture 40 hardens in approximately ten minutes for a typical spot size. Using larger or smaller spot sizes will affect the hardening time. Once the epoxy mixture hardens, it is removed using known methods such as by forceps. The hardened epoxy mixture has thus become a replicate 46 of the original surface.

Figure 4:
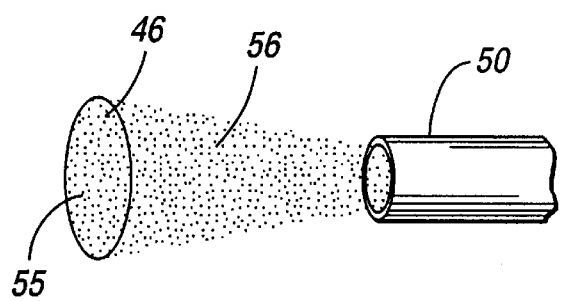
FIG. 4 shows a metal coating being applied onto a replicated surface.

A metal coating 55 is then applied to the replicated surface 46 using deposition (not shown) or sputtering technique as shown in FIG. 4. In the sputtering technique, a source of metal particles 50 emits metal particles 56 toward the replicated surface. The deposition technique involves evaporating a metal in a container with the replicated surface. The evaporated metal then deposits onto the replicated surface forming a thin layer. Other methods of applying a metal coating onto the replicated surface may also be used. The purpose of the metallic coating is to provide a reflective surface to the replicated surface 46. By using the metallic coating, the charcoal content becomes less critical and in some instances avoided entirely. The metallic coating can be any material that has reflective qualities but is preferably gold, aluminum, or silver. In order to view the minute details sought, the metallic coating is preferably between 10 and 90 angstroms thick, but more preferably between 20 and 40 angstroms thick.

Figure 5:
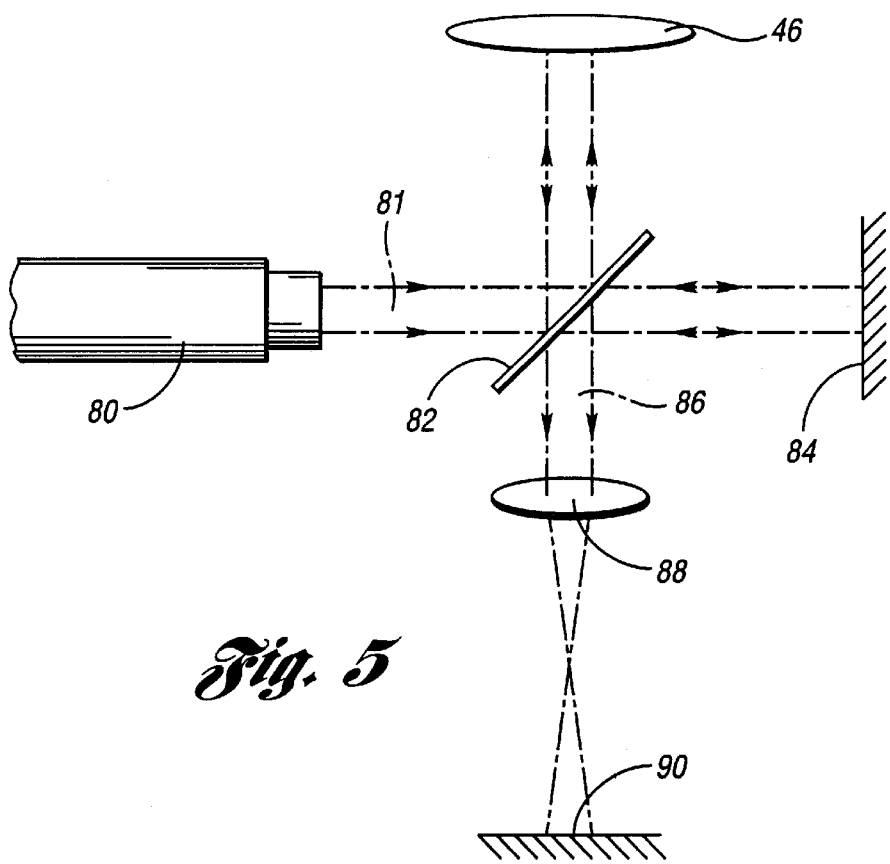
FIG. 5 shows the replicated surface being inspected using an interferometer.

Referring now to FIG. 5, the replicated surface 46 is shown being inspected in an interferometer. There are many different interferometers available. All interferometers measure the difference in the phase of light reflected from the specimen. One example illustrated in FIG. 5 is known as a Twyman-Green interferometer. A laser and beam expander 80 transmits a beam 81 approximately the size of the specimen to be tested. A beam splitter 82 allows a portion of the beam 81 to pass through onto a reference surface 84. Part of the beam 81 is reflected to the replicated surface 46 by the beam splitter 82. The beams 81 are reflected back from the reference surface 84 and the replicated surface 46 towards the beam splitter 82. The beam splitter 82 transmits the combined reflected beams 86 through an imaging lens 88 and a resulting interferogram 90 is formed. Using known formulas, the surface finish can be determined. The interferogram can be analyzed using a computer and color-coded diagrams showing the variations in the surface can be obtained. Other types of interferometers can be used. Commercially-available units from, for example, Wyko Corporation (now part of Veeco Corporation of Woodbury, N.Y.) and Zygo Corporation of Middlefield, Conn., are available.

Figure 6:
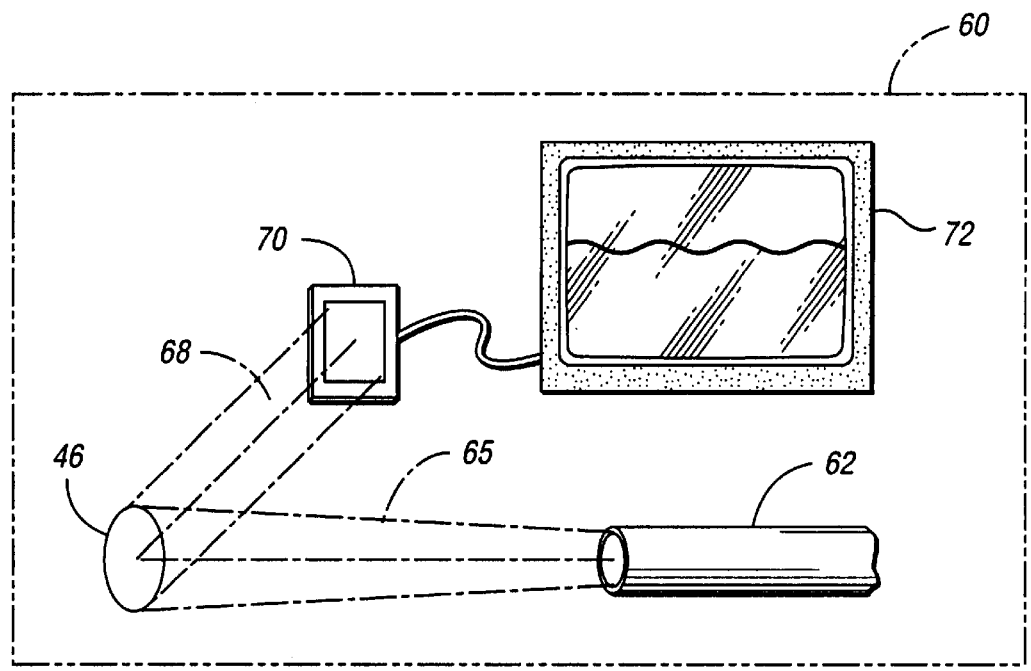
FIG. 6 shows the replicated surface being inspected using a scanning electron microscope.

Referring now to FIG. 6, the replicated surface 46 having a metal coating thereon is then put in an electron microscope 60. The electron microscope 60 comprises an electron gun 62 that shoots a beam of electrons 65 onto the replicated surface 46. Secondary electrons 68 are thrown off of the replicated surface 46 and are received by a receiver 70. The receiver 70 then causes a picture of the surface to be displayed on the display 72. A scanning electron microscope has a magnification of 5 to 500,000 times and a resolution of approximately 10 mm.

Optionally, the reflected surface can also be inspected using an optical microscope or a light sectioning microscope.

Although the technique has been described for use on a gear, it is equally applicable to other components having surfaces which are difficult to access or are inconvenient to bring to a laboratory for analysis. By using this technique, a sample may be non-destructively taken in the field and inspected in a laboratory later.

The technique may be used to inspect a variety of surfaces such as metal, plastic, or ceramic.

While embodiments of the invention have been illustrated and described, it is not intended that these embodiments illustrate and describe all possible forms of the invention. Rather, the words used in the specification are words of description rather than limitation, and it is understood that various changes may be made without departing from the spirit and scope of the invention.

What is claimed is:

1. A method of inspecting a hard-to-access surface finish of a component comprising:

providing an original surface on the hard-to-access surface;

applying release agent onto the original surface;

applying an epoxy over the release agent;

allowing the epoxy to harden into a replicated surface;

removing the replicated surface;

applying a metallic coating onto the replicated surface; and inspecting the coated replicated surface.

2. The method of claim 1 wherein the epoxy is a mixture comprising charcoal.

3. The method of claim 2 wherein the epoxy is a mixture comprising 5% or less charcoal by volume.

4. The method of claim 1 wherein applying a metallic coating comprises sputtering a metallic coating of gold or aluminum or silver.

5. The method of claim 1 wherein the metallic coating applied is 20 to 40 angstroms thick.

6. The method of claim 1 wherein the coated replicated surface is inspected using a scanning electron microscope.

7. The method of claim 1 wherein the coated replicated surface is inspected using an optical microscope.

8. The method of claim 1 wherein the coated replicated surface is inspected using an interferometer.

9. The method of claim 1 wherein the release agent is a petroleum distillate.

\* \* \* \* \*